United States Patent [19]

Wenig

[11] Patent Number: 4,729,997

[45] Date of Patent: Mar. 8, 1988

[54] NOVEL METHOD OF ADMINISTERING MECLIZINE TYPE PHARMACEUTICAL AGENTS AND NOVEL DOSAGE FORMS CONTAINING SAME

[75] Inventor: Jeffrey Wenig, Dix Hills, N.Y.

[73] Assignee: Nastech Pharmaceutical Co., Inc., N.Y.

[21] Appl. No.: 897,863

[22] Filed: Aug. 19, 1986

Related U.S. Application Data

[60] Division of Ser. No. 787,617, Nov. 15, 1985, Pat. No. 4,624,965, which is a continuation-in-part of Ser. No. 671,694, Nov. 11, 1984, abandoned, which is a continuation-in-part of Ser. No. 663,891, Oct. 23, 1984, abandoned.

[51] Int. Cl.$^4$ ............... A61K 31/44; A61K 31/47; A61K 31/54
[52] U.S. Cl. ................... 514/225; 514/294; 514/307
[58] Field of Search ............... 514/261, 225, 307, 294

[56] References Cited

U.S. PATENT DOCUMENTS 4,250,163 2/1981 Nagai .................... 424/28

FOREIGN PATENT DOCUMENTS 643756 2/1964 Belgium .
2230358 5/1974 France .

OTHER PUBLICATIONS

Rote Liste (1983), Solupen.

*Primary Examiner*—Stanley J. Friedman
*Attorney, Agent, or Firm*—Wyatt, Gerber, Shoup, Scobey and Badie

[57] ABSTRACT

Invention relates to nasal administration of known anti-nausea and anti-emetic therapeutic agents and dosage forms useful for such administration.

9 Claims, No Drawings

NOVEL METHOD OF ADMINISTERING MECLIZINE TYPE PHARMACEUTICAL AGENTS AND NOVEL DOSAGE FORMS CONTAINING SAME

RELATED APPLICATIONS

This application is a divisional application of application Ser. No. 787,617 filed Nov. 15, 1985, now U.S. Pat. No. 4,624,965, which is a continuation in part of application Ser. No. 671,694 filed Nov. 11, 1984, which is, in turn a continuation in part of application Ser. No. 663,891 filed Oct. 23, 1984. Both of the last mentioned of applications have been abandoned.

BACKGROUND OF INVENTION

1. Field of the Invention

The present invention relates to a novel method of administering anti nausea and anti emetic agents and to novel dosage forms containing such agents adapted for nasal administration.

The invention provides a novel method of administering therapeutic agents that inhibit nausea and emesis in mammals induced by stimulation of either the chemoreceptor trigger zone or the emesis (or vomiting) center in the central nervous system. Such stimulation can be caused by afferent stimulation (e.g., tactile pharyngeal impulses, labrynthine disturbances, motion, increased intracranial pressure, pain, distention of viscera or psuchologic factors) or blood borne emetic substances (e.g., as seen during pregnance, cancer chemotherapy, uremia, radiation therapy, electrolyte and endocrine disturbances, or the presence of chemical emetic substances).

The invention further provides dosage forms of those agents which are adapted for nasal administration and which include solutions, suspensions, sustained release formulations, gels and ointments. The therapeutic agents include selected antihistamines, anticholinergics, piperazines, phenothiazines, substituted butyprophenes and metoclopramide.

2. Background Art

A number of anti nausea and anit emetic agents are already known. Such agents are widely used therapeutically, chiefly in the treatment of emesis and nausea, and certain of the agents in the treatment of vertigo, motionsickness, hypersensitivity phenomena (anaphylaxis and allergy), rhinitis, sinusitis and gastroesophageal reflux disease. Unfortunately, many of these agents when used: [1] cause undesirable side effects, [2] are inefficiently and variably absorbed from current dosage forms, [3] are difficult or inconvenient to administer in the current dosage forms after the onset of emesis or nausea, and [4] have delayed onset of pharmacological activity when administered by current dosage forms. It has now been unexpectedly discovered that these pharmacologically active agents can be administered by nasal delivery to provide: enhanced bioavailability, minimized variations in blood levels, more rapid onset of activity and reduced dosages when compared to most current methods of administration (e.g., oral, subcutaneous, intra-muscular or by way of suppository).

Nasal delivery of therapeutic agents has been well known for a number of years. See, for example, U.S. Pat. Nos. 4,428,883; 4,284,648 and 4,394,390; and PCT application International Publication Number WO83/00286. See also, Hussain et al, *J. Pharm. Sci.:* 68, No. 8, 1196 (1979); 69 1240 (1980) and 69 1411 (1980).

The PCT document describes nasal compositions for the administration of scopalamine, a parasympathetic blocking agent but fails to teach or recognize that a therapeutic response can be elicited at a dosage level which is only a fraction of that normally employed.

It should also be mentioned that while nasal administration of certain therapeutic agents to mammals, especially humans is known, it is not a necessary conclusion from such knowledge that all therapeutic agents can be usefully administered by this route. In fact it has been shown that many drugs cannot be usefully administered by the nasal route. It certainly is not a suggestion that the selected anti-nausea and anit-emetic compounds of this invention which are not parasympathetic blocking agents can be usefully administered nasally to achieve enhanced bioavailability and sustained therapeutic blood levels.

SUMMARY OF INVENTION

It has been discovered that known anti nausea and anti emetic agents, the formulas of which are shown below can be usefully administered to mammals in novel compositions at extremely low dosage levels to elicit a systemic therapeutic response and to provide enhanced bioavailability, minimized variations in blood levels, more rapid onset of activity, ease of administration, and reduced side effects compared to most current methods of administration. Specifically, the blood levels of a therapeutic agent achieved by nasal administration can be substantially the same as the levels achievable with oral dosage units containing as much as ten times the amount of the same therapeutic agent. The nasal administration process of this invention is significantly more convenient than parenteral administration. Simple aerosol containers, or eye droppers which can be easily carried in a pocket or purse can be used for delivery. This should be compared with hypodermic needles which are difficult to use and repugnant to most people. In many jurisdictions it is illegal to transport them.

DETAILED DESCRIPTION OF THE INVENTION

The selected therapeutic agents for use in the compositions and methods of the present invention are brompheniramine, promethazine, cyproheptadine, dimenhydrinate, meclizine, cyclizine, chlorcyclizine, buclizine, trimethobenzamide, benzquinamide, metoclopramide, diphenhydramine, doxylamine, methapyrilene and tripelennamine.

Any pharmaceutically acceptable form of the therapeutic agents can be employed, i.e., the free base or a pharmaceutically acceptable salt thereof (e.g., cyclizine hydrochloride, cyclizine acetate, diphenhydramine hydrochloride, meclizine hydrochloride, promethazine hydrochloride, etc.) Generally the selected therapeutic agent is employed in the instant compositions and method in the pharmaceutically acceptable form which has previously been found most advantageous for oral or parenteral use. The structural formulae for certain of the free bases emcompassed by the present invention are set forth below:

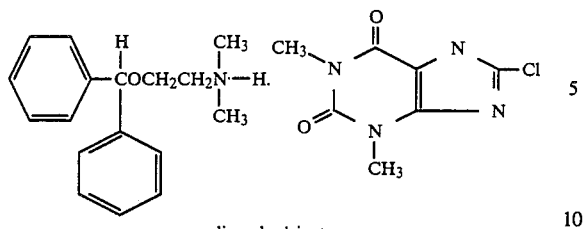
dimenhydrinate
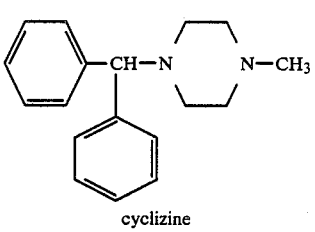
cyclizine
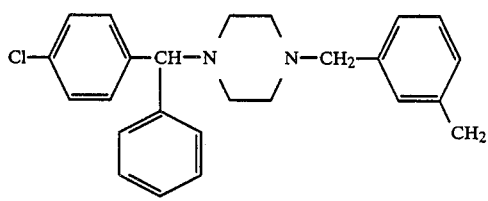
meclizine
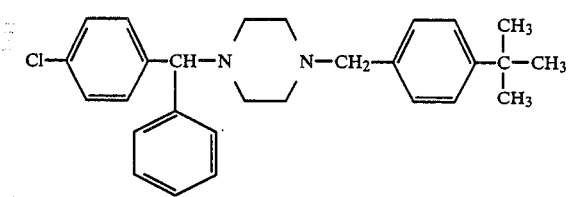
buclizine
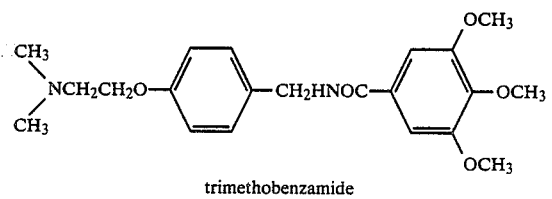
trimethobenzamide
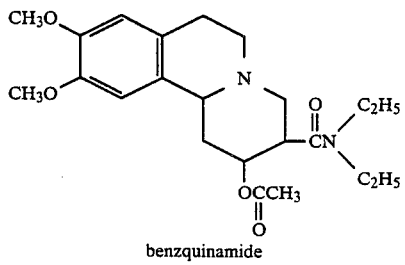
benzquinamide
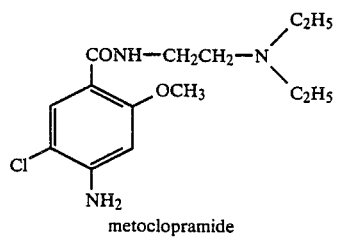
metoclopramide
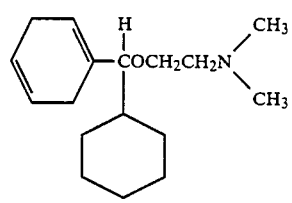
diphenhydramine
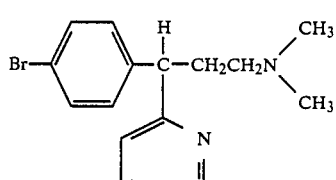
brompheniramine
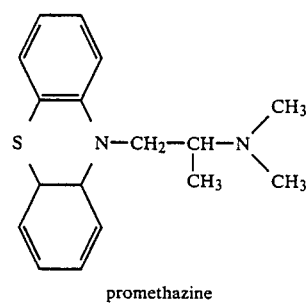
promethazine
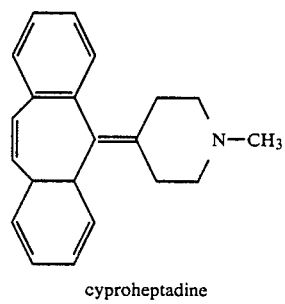
cyproheptadine
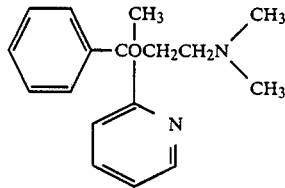
doxylamine
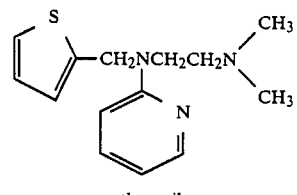
methapyrilene

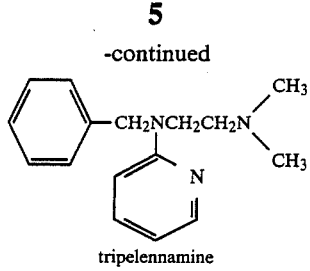
tripelennamine

These therapeutic agents and their methods of preparation are well known.

Cyclizine, chlorcyclizine, meclizine, and buclizine are all antihistimines and piperazine derivatives. They are referred to herein as the meclizine family and are preferred for use in this invention because of their ready availability and their high activity even at extremely low concentration. Metoclopramide is another preferred compound for use in this invention because when low dosages are administered nasally high blood levels are rapidly achieved and maintained for a long period of time.

In accordance with the present invention, the selected drugs named supra can be administered nasally to humans or other mammals with results considerably superior to those obtained with oral administration in terms of enhanced drug bioavailability and minimization of blood level variations, thus emabling use of these drugs at lower dosage levels than was previously possible except in the case of intravenous administration. It would appear that these selected drugs are rapidly absorbed from the nasal mucosa into systemic blood without first-pass metabolism.

Any of the selected drugs identified above can be conveniently administered nasally to warm-blooded animals to elicit a systemic, therapeutically anti-nausea or anit-emetic response by formulating it into a nasal dosage form comprising the desired drug, in a systemic, therapeutically effective anti-nausea or anti-emetic amount, together with a nontoxic pharmaceutically acceptable nasal carrier thereof. As indicated earlier, the drug can be employed in the form of the free base or in the form of a pharmaceutically acceptable salt. Suitable nontoxic pharmaceutically acceptable nasal carriers will be apparent to those skilled in the art of nasal pharmaceutical formulations. For those not skilled in the art, reference is made to the text entitled REMINGTON'S PHARMACEUTICAL SCIENCES, 14th edition, 1970. Obviously, the choice of suitable carriers will depend on the exact nature of the particular nasal dosage form required, e.g., whether the drug is to be formulated into a nasal solution (for use as drops or as a spray), a nasal suspension, a nasal ointment, a nasal gel or another nasal form. Preferred nasal dosage forms are solutions, suspensions and gels, which normally contain a major amount of water (preferably purified water) in addition to the active ingredient. Minor amounts of other ingredients such as pH adjusters (e.g., a base such as NaOH), emulsifiers or dispersing agents, buffering agents, preservatives, wetting agents and jelling agents (e.g., methylcellulose) may also be present.

Most preferably, the nasal composition is isotonic, i.e., it has the same osmotic pressure as blood serum. If desired, sustained release nasal compositions, e.g., sustained release gels, or when a more highly insoluble form is desired, a long chain carboxylic acid salt of the desired drugs can be conveniently employed. The carboxylic acid portion of the salt preferably contains 10 to 10 carbon atoms. Such salts (e.g., stearates, parmitates, etc.) can be readily synthesized, for example, by dissolving the hydrochloride salt of the drugs in water, then adding the alkali metal salt of the desired long chain carboxylic acid (e.g., sodium stearate). The corresponding long chain carboxylic acid salt which precipitates out of solution is removed by filtration. Alternatively, equimolar amounts of the drug free base and the long chain carboxylic acid are combined in methanol. That mixture is then added to a small volume of water, causing the desired salt (e.g., drug stearate) to precipitate out.

Those skilled in the art will be aware that a systemic, therapeutically effective anti-nausea or anti-emetic amount of a particular agent will vary with the particular agent, the age, size, weight and general physical condition of the patient. Typically the dosage level will be more similar to the expected dosage level for intravenous administration than to the dosage levels currently employed for other methods of administration, for example oral, rectal or subcutaneous.

As a practical matter the selected therapeutic compositions will normally be prepared in dosage unit forms to contain systemic, therapeutically effective amounts of the selected anti-nausea or anti-emetic agent. In specific instances fractions of the dosage units or multiple dosage units will be employed. Typically dosage units may be prepared to deliver 5 mg to 75 mg of therapeutic agent per 0.2 cc of solution or gel, these being the preferred types of compositions.

The following examples are given by way of illustration only and are not to be considered limitations of this invention many apparent variations of which are possible without departing from the spirit or scope thereof.

EXAMPLE 1

The following compositions are prepared as illustrative aqueous solutions of the named drugs suitable for use as nasal drops or nasal spray. In each case, the pH of the final composition is adjusted to 7.4 with NaOH. The solutions are adjusted to isotonicity with NaCL.

| Ingredient | Amount | |
|---|---|---|
| COMPOSITION A | | |
| diphenhydramine hydrochloride | 500 | mg |
| Tween 80 | 2 | mg |
| methylcellulose | 20 | mg |
| water, purified | 10 | ml |
| Final concentration 50 mg/0.2 cc | | |
| COMPOSITION B | | |
| dimenhydrinate | 2500 | mg |
| Tween 80 | 4 | mg |
| methylcellulose | 20 | mg |
| water, purified | 10 | ml |
| Final concentration 50 mg/0.2 cc | | |
| COMPOSITION C | | |
| metoclopramide hydrochloride | 500 | mg |
| Tween 80 | 2 | mg |
| methylcellulose | 20 | mg |
| water, purified | 10 | ml |
| Final concentration 10 mg/0.2 cc | | |

EXAMPLE 2

Two Sprague-Dawley male rats each weighing 250 to 300 grams, anesthetized using sodium pentobarbitol (50 mg/Kg of body weight), were administered nasally by micropipet a dosage level of 15 mg/Kg of body weight of the following composition:

216 mg metoclopramide.HCL (MCP.HCL)
292 mg 6.5% Tween 80 in Saline
895.2 mg polyethylene glycol (PEG 400)
522.2% mg polyethylene glycol (PEG 3350)
74.6 mg Stearyl-Alcohol The femoral artery was cannulated with heparinized polyethylene tubing (Clay Adams, PE-50) and blood samples were removed at the times indicated in Table 1.

The samples are analyzed by high pressure liquid chromatography (HPLC) as follows:

| Column: | Silica Column (4.6 × 250 mm) |
|---|---|
| Detection: | 308 nm |
| Mobile Phase: | $CH_2Cl_2:MeOH:NH_4OH = 90:10:0.5$ |
| Flow Rate: | 1.7 ml/min |

Plasma (0.3 ml) was placed in a test tube and 0.1 ml of 1N NaOH was added. Four ml of methylene chloride was then added and the mixture shaken for 10 minutes on a reciprocal shaker, centrifuged for 3 minutes in an IEC clinical centrifuge and the upper layer removed by aspiration. A 3.0 ml aliquot of the methylene chloride layer was transferred to a second table and evaporated to dryness with a stream of nitrogen gas. The resulting residue was then dissolved in 0.1 to 0.5 ml of mobile phase and submitted to HPLC analysis.

The results are shown in Table 1.

| Nasal Absorption (Nasal Formulation) | |
|---|---|
| Time (min) | Concentration* ($\mu$g/ml plasma) |
| 0 | 0 |
| 5 | 0.96 ± 0.12 |
| 10 | 1.41 ± 0.10 |
| 15 | 1.61 ± 0.23 |
| 30 | 1.55 ± 0.18 |
| 45 | 1.30 ± 0.18 |
| 60 | 1.26 ± 0.3 |
| 75 | 1.11 ± 0.34 |
| 90 | 1.04 ± 0.35 |
| 120 | 1.10 ± 0.38 |
| 180 | 1.09 ± 0.36 |
| 240 | 0.94 |

*Mean ± S.D. (n = 3)

It will be noted that the concentration is measurable after only 5 minutes, reaches maximum concentration in 15 minutes and sustains a high level for at least 4 hours.

EXAMPLE 3

The procedure of Example 2 was repeated with three rats except that the MCP.HCL was administered at the same dosage level in isotonic sodium chloride. The results are shown in Table 2.

| Nasal Absorption (Solution - Saline) | |
|---|---|
| Time (min) | Concentration* ($\mu$g/ml plasma) |
| 0 | 0 |
| 5 | 0.42 ± 0.05 |
| 10 | 0.68 ± 0.10 |
| 15 | 0.85 ± 0.12 |
| 30 | 1.37 ± 0.21 |
| 45 | 1.51 ± 0.18 |
| 60 | 1.61 ± 0.05 |
| 75 | 1.62 ± 0.17 |
| 90 | 1.63 ± 0.18 |
| 120 | 1.55 ± 0.26 |
| 150 | 1.55 ± 0.21 |
| 240 | 1.29 ± 0.28 |

*Mean ± S.D. (n = 3)

It will be observed that the time to achieve maximum levels was extended, but that the high levels were maintained for a longer period of time.

EXAMPLE 4

A female beagle dog weighing about 10 Kg was anesthetized with sodium pentobarbitol (30 mg/kg of body weight).

The following composition was administered to the nasal cavity using a syringe at a dose of 10 mg of MCP:
50 mg of MCP
200 mg of 5% Tween 80
430 mg of PEG 400
280 mg of PEG 3350
40 mg of stearyl alcohol A catheter was inserted into the cubital vein and the blood samples were collected at the indicated times shown in the following Table 3.

The samples were analyzed by HPLC as follows:

| HPLC Analysis | |
|---|---|
| Column | Silica column (Altex 4.6 × 250 mm) |
| Detection | 308 nm |
| Mobile Phase | $CH_2Cl_2:MeOH:NH_4OH = 90:10:0.5$ |
| Flow Rate | 1.7 ml/min |

Plasma (2.0 ml) was placed in a test tube and 0.5 ml of 1N NaOH was added. Seven ml of methylene chloride was then added and the mixture was shaken for 10 min on a reciprocal shaker, centrifuged at 2000 rpm for 3 min, and the upper layer was removed by aspiration.

A 6.0 ml of aliquot of the methylene chloride was transferred to a second tube and evaporated to dryness with a stream of nitrogen gas. The resulting residue was then dissolved in 0.4 ml of mobile phase and submitted to HPLC analysis.

TABLE 3

| Nasal-Absorption | |
|---|---|
| Time (min) | Concentration (ng/ml plasma) |
| 0 | 0 |
| 5 | 48.1 |
| 10 | 62.5 |
| 15 | 78.6 |
| 30 | 90.5 |
| 60 | 112.7 |
| 90 | 102.8 |
| 120 | 84.2 |
| 180 | 82.0 |
| 240 | 72.2 |
| 300 | 56.9 |
| 360 | 53.1 |

EXAMPLE 5

The procedure of Example 4 was repeated except that the MCP.HCL was administered at the same dosage level in isotonic sodium chloride. The results are shown in Table 4.

TABLE 4

Nasal Absorption
(Solution-Saline)

| Time | Concentration (ng/ml plasma) |
| --- | --- |
| 0 | 0 |
| 5 | 74.4 |
| 10 | 98.9 |
| 15 | 150.8 |
| 30 | 162.8 |
| 60 | 103.6 |
| 90 | 90.5 |
| 120 | 68.2 |
| 180 | 60.8 |
| 240 | 49.1 |
| 300 | 38.4 |
| 360 | 34.2 |

EXAMPLE 6

Seven Wistar rats weighing from 250 to 275 gr (Charles River Laboratories, Inc., Wilmington, MA) were anesthetized with 50 mg/kg i.p. sodium pentobarbitol. The neck was surgically opened, and a polyethylene tube (PE 260, Intramedic Clay Adams) was inserted into the trachea and tied in place. Another PE tube was inserted into the esophagus to the posterior of the nasal cavity and also secured. The juglar veins were exposed and the nasopalatine was closed with glue (Super Glue, Woodhill Permetex, Cleveland, OH). Meclizine dihydrochloride at a concentration of 6.4 mg/ml in normal saline containing 2% Tween 80 was injected at dosage levels of 0.64 mg/rat and 1.28 rat by syringe through the tube into the nasal cavity. Blood (0.2–0.3 ml) was sampled at various times from the juglar veins, alternating left and right, and stored on ice in preheparinized microfuge tubes.

Extraction of meclizine from whole blood was performed by the method of Hom and Ebert. *J. Pharm. Sci* 66: 710 (1977). Briefly, whole heparinized blood was centrifuged on a Beckman Microfuge B, and 0.1 ml of plasma collected. One normal HCL (0.4 ml) was added to this in another microfuge tube, and the mixture was vortexed for 30 seconds. One ml of chloroform was then added, the samples vortexed for an additional minute, and then centrifuged again. The entire chloroform phase was removed, transferred to a test tube, and evaporated to dryness with a Buchler Evapomix. The extract was resuspended in 0.2 ml of HPLC solvent and duplicate samples were injected into the HPLC for analysis.

For HPLC a Waters Corp., Milford, MA, system was utilized. This consisted of models 720 B WISP autosampler, both 480 Lamda-Max variable and 440 dual-channel UV detectors, 660 solvent programmer, 730 data module, M6000A and M-45 pumps, and a 3.9×150 mm Novapak $C_{18}$ column (5 m particle size) preceded by a 3.9×23 mm Corasil (particle size, 30–38 m) $C_{18}$ filled guard column. The conditions for HPLC were isocratic 23:77 0.1M sodium acetate (PH 4.3) methanol, flow rate 1.0 ml/min and detection at 232 nm.

The results of the analysis are shown in Table 5.

TABLE 5

Nasal-Absorption

| Time (min) | Concentration (ng/ml plasma) | |
| --- | --- | --- |
| | 0.64 Dosage | 1.28 Dosage |
| 2 | 70 | 210 |
| 4 | 250 | 720 |
| 6 | 300 | 960 |
| 8 | 630 | 1100 |
| 15 | 620 | 970 |
| 30 | 440 | 720 |
| 45 | 250 | 530 |
| 60 | 230 | — |
| 75 | 210 | — |
| 90 | 190 | 340 |
| 120 | 110 | — |
| 150 | 100 | 180 |
| 180 | 80 | — |
| 210 | 70 | 120 |
| 240 | 70 | — |

EXAMPLE 7

Toxicity Studies in Rabbits

A group of twenty rabbits were divided into 14 test and 6 control animals. The test animals were administered 20 mg of the following gel composition:

| Formulation to make 100 ml at 100 mg/cc | |
| --- | --- |
| BENZYL ALCOHOL N.F. | 1.500 ml |
| SODIUM CHLORIDE | 0.800 grams |
| METHOCEL 4000 U.S.P. | 2.000 grams |
| ACETIC ACID N.F. | 0.320 grams |
| SODIUM ACETATE U.S.P. | 0.077 grams |
| SORBITOL SOLUTION U.S.P. | 5.000 ml |
| METOCLOPRAMIDE HCL | 10.000 grams |
| WATER PURIFIED U.S.P. q.s. | 100.000 ml | by nasal instillation at 8, 12 and 16 hours for a total of fourteen days. The control animals were similarly treated with isotonic saline solution.

Animals administered the metoclopramide gel formulation gained weight over the 14 days of the test period. No significant clinical observations were noted among the test animals, and treated nostrils appeared normal at all times, as compared to the untreated nostrils. Similar results were found among animals receiving the saline control solution.

Histopathological examination of the nasal cavities of animals sacrificed at 24 hours, 7 days and 14 days after initiation of the test, revealed no lesions which could be attributed to treatment with the test formulation. Nasal mucosal inflammation and exudate accumulation were no greater than normal background findings, and rhinitis was not higher than anticipated in conventional rabbits. Hemorrhage or blood present in the nasal cavity was considered postmortem hemorrhage. Other lesions were considered normal background lesions, not directly attributed to the test formulation.

Two animals died on test. The death of one rabbit from the control group was attributed to mucoid enteropathy, a common malady in laboratory rabbits. The death of the rabbit from the test group was tentatively attributed to intussusception, not an uncommon finding in rabbits. There was no evidence for an association between the administration of the test formulation and the death of this animal.

Examination of the nasal cavities from rabbits administered the formulation containing metoclopramide revealed no lesions which could be attributed to treatment with the test composition. The treated nasal cavities were not significantly different from untreated reference nasal cavities, or from those treated with the saline control.

EXAMPLE 8

A 4-way crossover study was conducted in eight volunteer human subjects to compare the effects of the nasal administration of 5 and 10 mg of metoclopramide hydrochloride in a gel formulation, 10 mg of the same agent in an oral formulation and 5 mg of the product intramuscularly. The nasal formulation had the following composition:

| Formulation to make 100 ml at 100 mg/cc | |
|---|---|
| BENZYL ALCOHOL N.F. | 1.500 ml |
| SODIUM CHLORIDE U.S.P. | 0.800 grams |
| METHOCEL 4000 U.S.P. | 2.000 grams |
| ACETIC ACID, N.F. | 0.320 grams |
| SODIUM ACETATE U.S.P. | 0.077 grams |
| SORBITOL SOLUTION U.S.P. | 5.000 ml |
| METOCLOPRAMIDE HCL | 5.000 grams |
| WATER PURIFIED U.S.P. q.s. | 100.000 ml |

The oral and intramuscular compositions were commercial formulations available from A. H. Robbins Pharmaceutical Company, Richmond, VA. under the name Reglan.

Substantially equivalent maximum blood levels were achieved with the 10 mg nasal, 10 mg P.O. and 5 mg I.M. The pharmacokinetic profiles for these doses were statistically identical. No evidence of local toxicity was observed during or after the study.

The results are shown in the following table:

TABLE 6

COMPARISON OF PLASMA CONCENTRATIONS, PEAK CONCENTRATIONS, TIME TO PEAK AND ELIMINATION RATE CONSTANTS ($K_{el}$) FOLLOWING THE ADMINISTRATION OF METOCLOPRAMIDE HCL ORALLY (PO) 10 MG, INTRAMUSCULARLY (IM) 5 MG, AND INTRANASALLY (IN) 5 AND 10 MG IN HUMAN SUBJECTS (n = 8)

|  | PO | IM | 5 IN | 10 IN |
|---|---|---|---|---|
| Peak Concn. (ng/ml) | 36.0(7.3) | 34.0(3.3) | 15.2(5.4) | 35.1(7.6) |
| Time to Peak (min.) | 97.5(21.2) | 91.9(39.6) | 80.6(36.7) | 131.3(39.1) |
| $K_{el}$ (K10$^3$) | 1.89(1.13) | 2.67(1.00) | 2.59(1.41) | 2.77(1.26) |

The study was extended to dosage levels of 20 mg and 40 mg by the intranasal route using the same compositions. Useful blood levels were achieved. There was no evidence of either local or systemic toxicity in the human subjects either before or after completion of the study.

EXAMPLE 9

H.F. was a 55 year-old female with Stage IV ovarian cancer. The patient failed conventional chemotherapy and developed a complete bowel obstruction secondary to tumor growth in February, 1985.

Because of repeated nausea and vomiting due to bowel obstruction and other factors, intranasal metoclopramide at 40 mg per dose every four hours was employed for control of symptoms. The intranasal metoclopramide contained her nausea between occasional bouts of vomiting which were inevitable secondary to the mechanical bowel obstruction. The patient had previously not responded to anti-emetic suppositories given for nausea.

The formulation of the gel compositions was the same as in Example 7.

The study was extended to five more cancer patients who were previously refractory to other antinausea treatments with the same formulation and same dosage schedule. All patients benefited from the treatment and four preferred this route of administration over intraveneous injections.

What is claimed is:

1. A method of eliciting a systemic, therapeutic, antihistaminic, antinausea or antiemetic response in a mammal which comprises nasal administration to said mammal of a systemically, therapeutically effective antihistaminic antinausea or antiemetic amount of a therapeutic agent selected from the group consisting of cyclizine, chlorcyclizine, meclizine, buclizine, trimethobenzamide and benzquinamide or a pharmaceutically acceptable acid addition salt thereof together with a pharmaceutically acceptable nasal carrier therefor.

2. A method as in claim 1 wherein the pharmaceutically acceptable salt is a salt of a carboxylic acid containing from about 10 to 20 carbon atoms.

3. A method as in claim 1 wherein the therapeutic agent is cyclizine, chlorcyclizine, meclizine or buclizine.

4. A pharmaceutically acceptable composition for nasal administration in the form of a nasal solution, suspension, ointment or gel to obtain a systemic, therapeutic, antihistaminic antinausea or antiemetic response in a mammal comprising a systemically, therapeutically effective amount of an antihistaminic, antinausea or antiemetic therapeutic agent selected from the group consisting of cyclizine, chlorcyclizine, meclizine, buclizine, trimethobenzamide and benzquinamide or a pharmaceutically acceptable acid addition salt thereof together with a pharmaceutically acceptable nasal carrier therefor.

5. A composition as in claim 4 wherein the pharmaceutically acceptable salt is a salt of a carboxylic acid containing from about 10 to 30 carbon atoms.

6. A composition as in claim 4 wherein the therapeutic agent is cyclizine, chlorcyclizine, meclizine or buclizine.

7. A composition as in claim 4 in dosage unit form.

8. A composition as in claim 5 in dosage unit form.

9. A composition as in claim 6 in dosage unit form.

* * * * *